United States Patent [19]

Lindström

[11] Patent Number: 5,969,160

[45] Date of Patent: Oct. 19, 1999

[54] PROCESS FOR PRODUCING PHTHALIC ANHYDRIDE

[75] Inventor: Jan Lindström, Nol, Sweden

[73] Assignee: Neste Oy, Espoo, Finland

[21] Appl. No.: 09/021,749

[22] Filed: Feb. 11, 1998

[30] Foreign Application Priority Data

Feb. 25, 1997 [SE] Sweden ................................. 9700655

[51] Int. Cl.⁶ .................................................. C07D 307/89
[52] U.S. Cl. ............................................................... 549/248
[58] Field of Search ............................................. 548/248

[56] References Cited

FOREIGN PATENT DOCUMENTS

| 9201926 | 8/1993 | Australia . |
| 0 453 951 A1 | 4/1991 | European Pat. Off. . |
| 0 686 633 A1 | 4/1995 | European Pat. Off. . |

*Primary Examiner*—Bernard Dentz
*Attorney, Agent, or Firm*—Merchant & Gould P.C.

[57] ABSTRACT

Process for producing phthalic anhydride by catalytic gaseous phase oxidation of o-xylene or naphthalene in the presence of catalyst, whereby the reaction is carried out in at least two separate reactors. The first reactor is a salt-cooled main reactor and the second reactor is a post-reactor without cooling means containing same or different catalyst as the first reactor, wherein the feed flow to the post reactor consists of only gaseous effluent from the first reactor and the gas flow in the second reactor takes place from up to down without saltbath cooling.

5 Claims, No Drawings

PROCESS FOR PRODUCING PHTHALIC ANHYDRIDE

The present invention concerns manufacturing phthalic anhydride by partial oxidation of o-xylene or naphthalene.

BACKGROUND OF THE INVENTION

Phthalic anydride is manufactured industrially by gaseous oxidation of o-xylene by passing the o-xylene/air mixture through a tube reactor, where the tubes are filled with catalyst that contain vanadiumpentoxide and titanium oxide. In the partial oxidation of orthoxylene or naphtalene to phthalic anhydride it is very important to obtain highest possible hydrocarbon load, with still good quality coming out from the reactors.

In order to optimize the catalyst, it is very important to control the reaction in the way to achieve highest possible hydrocarbon load ($g/Nm^3$) to be converted into best possible quality at highest possible yield. Depending on the type of catalyst (activity and selectivity) the possibilities will vary rather wide with existing catalysts on the market. All existing catalysts are based on vanadium pentoxide and different moderators are involved to make the different catalysts to operate differently concerning sensitivity, activity and selectivity.

To control the reaction and the activity of the catalyst, it is very important to keep the saltbath at the right temperature. The bath is flowing around the tubes in order to remove the heat created from the reaction inside the tubes, which are filled with catalyst. Normally the saltbath temperature will be in the range of 370–400° C. over the life-time of the catalyst. To be able to produce a good quality the reaction inside the tubes must be held at a rather high temperature level (450–470° C.) which means that a lot of byproducts will be created (specifically oxidation products like CO, $CO_2$ and maleic anhydride) which are the biggest impurities in this reaction by weight. That fact will reduce the yield from hydrocarbon to phthalic anhydride and furthermore at these high temperature conditions it would be very difficult to hold the reaction "steady" and to optimize the reaction conditions.

During recent years the development has moved towards higher hydrocarbon load ($g/Nm^3$) while the reactors today look very much the same as in the past. The producers of catalysts have tried to compensate these higher loads by changing the recipes.

New catalysts have been introduced which are splitted in the activity in the way that reaction (temperature profile) will be more spread out over the reaction tubes, but still the reaction will be very sensitive to variations and of course very much depending on the quality of the catalyst (activity, selectivity). This means that today it can be very difficult to operate the reactors with high load and good quality because the sensitivity of the oxidation has increased.

Another way to overcome the difficulties is the use of two or more reactors instead of one reactor. Such solution is disclosed in EP-patent application 0686633. According to this application two reactors are applied and the gas composition at the inlet of the first reactor is controlled in the range of the lower inflammability limit, while the gas composition at the inlet of the second reactor is controlled closer to the range of the upper limit of inflammability. Both reactors and more specifically the second reactor are preferably tubular reactors cooled by molten salt circulation. The tubes of the second reactor are substantially longer than the tubes of the first reactor. The reactors are applied so that feedstock is added also to the effluent of the first reactor and the gas mixture is then introduced into the second reactor. Providing two reactors which are both salt-cooled leads to high investment and operating costs and besides, in existing plants available space is often limited.

A reference is made also to European patent application 0453951, where the reactor is divided two or more reaction zones following each other and by using same or different catalyst in each zone. Also in Austrian patent application 9201926 a second reaction zone is disclosed. In this case the effect obtained by said construction is insufficient and requires specially manufactured honeycomb catalyst structures.

BRIEF DESCRIPTION OF THE INVENTION

According to the invention a better process for producing phthalic anhydride is found, in which two reactors are used in a different way. Thus the invention concerns a process for producing phthalic anhydride by catalytic gaseous phase oxidation of o-xylene or naphthalene in the presence of vanadium pentoxide catalyst. The invention is characterized in that the reaction is carried out in two separate reactors, whereby the first reactor is a salt-cooled reactor and the second reactor contains the same or different commercially available catalyst as the first reactor, the feed flow consists of only gaseous flow coming from the first reactor, and the gas flow in the second reactor takes place from up to down without saltbath cooling.

The second reactor or post-reactor is a fixed bed reactor which works adiabatic with the same or different type of catalyst compared to the main reactor. Through utilizing post-reactor technique the reaction in the main reactor can be controlled in the way that optimum conditions will be achieved even at very high loads. At the same time non-wanted reaction products from main reactor will be transformed adiabatically in the post-reactor and controlled to decided level (phthalide content decreases and some aromates will be combusted).

Through this way being able to change the condition in the oxidation process, several important advantages can be obtained. By using post-reactor the oxidation system can be loaded very high, because the main reactor can be operated in underoxidation conditions by lowering reactor temperature. The amount of phthalide formed will be higher but it can be controlled down to extremely low levels in the post-reactor. A lower salt-bath temperature in the main reactor gives a better temperature configuration over the reaction zone thus avoiding hot-spot temperatures which lower combustion of o-xylene to CO and $CO_2$. By using a post-reactor the product quality and the yield will be improved and the life-time of the catalyst will be prolonged. Further, it is important to point out that by use of a post-reactor connected outside the main reactor is not only a cost-effective way to get the benefits mentioned above but also big advantages will be achieved if modifications are necessary. Thereby it will be easy to bypass and stop the reactor and make changes like different catalyst bed height or changing type of catalyst. These operations can be done in a very short time (<12 h). If only one reactor is used, it takes several days to cool down and several days to heat-up again. Production losses will thereby be small when modifications are needed in the post-reactor.

DETAILED DESCRIPTION OF THE INVENTION

The feedstock for the production of phthalic anhydride is o-xylene, naphthalene or a mixture of o-xylene and naphthalene. The oxidation air required for the conversion of the o-xylene into phthalic anhydride is drawn in from the atmosphere and filtered in the oxidation air filter. The clean air is then compressed in a blower up to the pressure which represents the flow resistance of the plant.

The oxidation air is preheated to about 180° C. and then charged with feedstock in concentrations up to 90 g o-x/Nm$^3$ air. The air rate is typically 4 Nm$^3$ per reactor tube and hour.

The o-xylene is injected and mixed with the process air in a mixer of special design by means of spray nozzles in a venturi-pipe arranged and designed for optimum distribution and vaporization of the o-xylene in the air stream.

The equipment handling the explosive mixture is designed and equipped with safety devices in a way that any damage for the equipment or personnel can be excluded once a deflagration should occur. The plant is designed to make an ignition of flammable material extremely unlikely.

After mixing, the feedstock/air mixture enters the tube type reactor. The reactor tubes are filled with catalyst, which is a ring-type catalyst coated with vanadium pentoxide and titanium dioxide. The reactor is cooled by a circulating salt melt which controls the temperature. The salt bath is cooled in a salt bath cooler by producing steam.

The reaction temperature inside the tubes is kept at high temperature level in order to produce good product quality. Thus the reaction temperature would normally be in the range of 450–470° C. over the lifetime of the catalyst. The second reactor according to the invention makes possible that the temperature in the first reactor could be lowered towards under oxidation conditions, which means that the saltbath temperature will be some 5–10° C. lower compared to normal conditions. Thus the reaction temperature inside the reaction tubes will be lowered by 40–50° C. which will stabilize the conditions in the reaction zone, but at the same time there will be formation of undesired reaction products like phthalide up to 10 times higher than normal (0.1→1.0 w-%). The way to control how long to go in underoxidation is to control the reaction gas with so-called "orthoxylene slippage", which means unreacted orthoxylene passing the main reactor. When orthoxylene concentration reaches >100 ppm the limit is nearby. This reaction gas coming from the main reactor contains comparably low content of overoxidation products (MA, $CO_x$) but with high amount of underoxidation products like phthalide.

The reactor effluent gas leaving the reactor is passing the post-reactor, which is used without cooling. Before entering the second reactor the gas could be cooled down in order to control the adiabatic temperature rise which will occur by reaction in the adiabatic post-reactor bed. Specially important to cool the gas will be at the end of the catalyst life-time when the temperature of the reaction gas is very high. Above about 420° C. the combustion of phthalic anhydride in the post-reactor begins to be considerable.

Therefore, according to one embodiment of the invention a cooler is used between the reactors in order to control the temperature. The cooler can also be useful in order to control the temperature in case that different kind of catalyst is used in the main reactor and the post-reactor.

In the post-reactor containing catalyst the transformation of phthalide to phthalic anhydride will take place, together with other reactions like transformation of rest parts of orthoxylene to phthalic anhydride, and some aromates will be burned. Also a minor part of phthalic anhydride will be burned to $CO_x$, which means that the yield will go down while passing the post-reactor, but as the yield in the gas before the post-reactor is higher than in normal reactors, an increase of the total yield at the exit of the second reactor will be obtained, compared with a normal reactor under same conditions.

The optimum conditions will be achieved when the adiabatic delta temperature in the post-reactor is 10–° C., depending on what kind of catalyst is used.

The catalyst in the post-reactor can be same or different catalyst as in the main reactor. As catalyst normal ring-type catalysts having a diameter of 7–8 mm may be used. The catalyst is packed on a perforated support plate.

The flow of gas into the post-reactor according to the invention is carried out from up to down. Thus the catalyst is placed at or near the bottom of the reactor without danger that some catalyst would follow with the reactor effluent away from the reactor.

After the post reactor the effluent is then gradually cooled in a suitable way, for example by using one or more gas/oil exchangers and gas coolers of tubular design producing steam.

The reactor effluent gas leaving the gas coolers is further cooled down in the fin tube switch condensers, for example several condensers in parallel. By cooling the gas the crude phthalic anhydride desublimates on the fin surface.

Every switch condenser is designed to be loaded with a certain quantity of crude phthalic anhydride. After loading, the unloading is performed by isolating two switch condensers from the gas stream and heating it up to melt the crude phthalic anhydride from the fin tubes. The crude phthalic anhydride is collected in the crude phthalic anhydride tank, from where it is continuously pumped to the purification section.

The switch condensers are cooled and heated in a predetermined sequence by an electronic timer and monitoring system so that during a full cycle each switch condenser will have been loaded and unloaded once.

The tail gas left over after desublimation contains still small amounts of product and mainly by-products.

The continuous purification of PA can be carried out by ordinary way by distillation. Before distillation the crude phthalic anhydride may be subjected to heat treatment. This pretreatment serves for dehydration of any phthalic acid formed during desublimation as well as the conversion of by-products into compounds which are separable in the distillation. Addition of sodium carbonate during the pretreatment can improve the color stability of the pure phthalic anhydride by inducing polymerisation of aldehydes with MA and phthalic anhydride.

EXAMPLE

A commercial reactor with 1800 tubes, diameter of 25 mm and length of 3 m was used for production of phthalic anhydride. The reactor had a height of 6 m and a diameter of 2.3 m. The system was equipped with an uncooled post-reactor, which had a height of 5 m and a diameter of 1.3 m. From the inside volume of the post-reactor 1 m$^3$ was used for catalyst bed. As catalyst vanadium pentoxide was used. The feed consisted of liquid orthoxylene with a purity of at least 98 w-%, which was sprayed and mixed with air before the main reactor. The reactor load was 80 g o-x/Nm$^3$. The salt-bath temperature was 385° C. and the temperature increase over the post-reactor was 21° C.

The analysis before and after the post-reactor is presented in the table below.

|  |  | % MA | % CA | % BA | % PA | % PHT |
|---|---|---|---|---|---|---|
| Beginning of test run | Before post-reactor | 2.55 | 0.60 | 0.32 | 95.45 | 0.51 |
|  | After post-reactor | 3.17 | 0.40 | 0.36 | 95.91 | 0.06 |
| After one week | Before post-reactor | 2.56 | 0.66 | 0.40 | 94.77 | 0.78 |
|  | After post-reactor | 3.03 | 0.42 | 0.47 | 95.87 | 0.08 |
| After two weeks | Before post-reactor | 2.54 | 0.62 | 0.43 | 94.64 | 0.89 |
|  | After post-reactor | 2.70 | 0.41 | 0.43 | 96.29 | 0.08 |

MA = maleic anydride, CA = citraconic acid, BA = benzoic acid, PA = phthalic anhydnde, PHT = phthalide

I claim:

1. Process for producing phthalic anhydride by catalytic gaseous phase oxidation of o-xylene or naphthalene in the presence of catalyst, characterized in that the reaction is carried out in a first reactor and a second reactor, and a cooler is placed between the first reactor and the second reactor, wherein the first reactor is a salt-cooled main reactor and the second reactor is a post-reactor without cooling means containing same or different catalyst as the first reactor, wherein the feed flow to the post reactor consists of only gaseous effluent from the first reactor and the gas flow in the second reactor takes place from up to down without saltbath cooling, and wherein the gaseous effluent from the first reactor is cooled in the cooler.

2. Process according to claims 1 characterized in that as catalyst a supported vanadium oxide or titanium dioxide catalyst in the form of rings having a diameter of 7–8 mm and lenght of 10–80 mm is used.

3. Process according to claim 1, characterized in that the main reactor is operated in underoxidation conditions in such degree that the orthoxylene content in the effluent is not greater than 100 ppm.

4. Process according to claim 1, characterized in that an adiabatic delta temperature of 10–20° C. is kept in the post-reactor.

5. Process according to claim 1, characterized in that the temperature in the main reactor is kept 40–50° C. lower than the optimum temperature necessary to carry out the reaction without a post-reactor.

* * * * *